United States Patent
Tararine

[19]

[11] Patent Number: 6,057,551
[45] Date of Patent: May 2, 2000

[54] PROCESS FOR PROCESSING PULSES DELIVERED BY A GAMMA CAMERA AND A GAMMA CAMERA USING THIS PROCESS

[75] Inventor: Michel Tararine, Sceaux, France

[73] Assignee: SMV International, Buc Cedex, France

[21] Appl. No.: 08/925,226

[22] Filed: Sep. 8, 1997

[30] Foreign Application Priority Data

Sep. 9, 1996 [FR] France .................................. 96 11102

[51] Int. Cl.[7] ........................... G01T 1/164; G01T 1/172
[52] U.S. Cl. ...................................... 250/363.03; 250/369
[58] Field of Search ......................... 250/363.03, 363.04, 250/363.02, 363.07, 369, 370.08, 370.09

[56] References Cited

U.S. PATENT DOCUMENTS

| | | |
|---|---|---|
| 3,011,057 | 11/1961 | Anger . |
| 4,057,727 | 11/1977 | Muehllehner ........................ 250/363.03 |
| 5,276,615 | 1/1994 | Tournier Edmond et al. ......... 378/120 |
| 5,373,161 | 12/1994 | Tararine .............................. 250/363.09 |
| 5,585,637 | 12/1996 | Bertelsen et al. .................... 250/363.03 |
| 5,606,166 | 2/1997 | Tararine .............................. 250/363.07 |

FOREIGN PATENT DOCUMENTS 0 470 909  2/1992  European Pat. Off. ............... 378/120

OTHER PUBLICATIONS

D.A. Mankoff et al., The High Count Rate Performance of a Two–Dimensionally Position–sensitive Detector for Position Emission Tomography, Physics In Medicine and Biology, vol. 34, No. 4, Apr. 1989.

*Primary Examiner*—Constantine Hannaher
*Assistant Examiner*—Albert Gagliardi
*Attorney, Agent, or Firm*—Nilles & Nilles SC

[57] ABSTRACT

A process for processing signals delivered by a gamma camera including two detectors (23, 26, 28, 24, 27 and 29) on either side of a radioactive body (25), each of the detectors (23, 26, 28, 24, 27 and 29) producing analogue electric signals ($x^+$, $x^-$, $y^+$, $y^-$ and w) consisting of pulses relevant to the impacts of gamma-ray photons ($\gamma'$ and $\gamma''$) on the detectors (23 and 24), the coordinates of the impact points being calculated from compressed signals, and the detection of the impact being performed in parallel by coincidence.

14 Claims, 5 Drawing Sheets

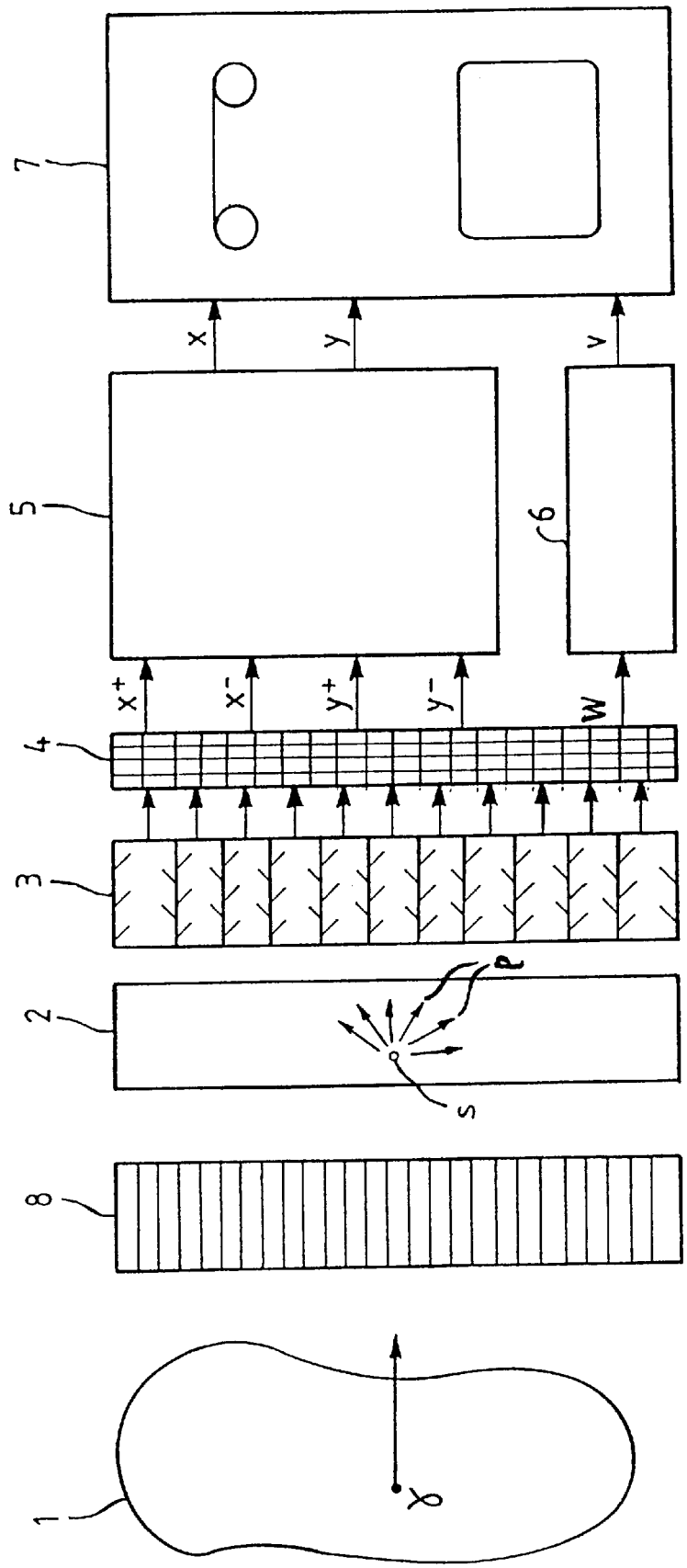
FIG_1
PRIOR ART

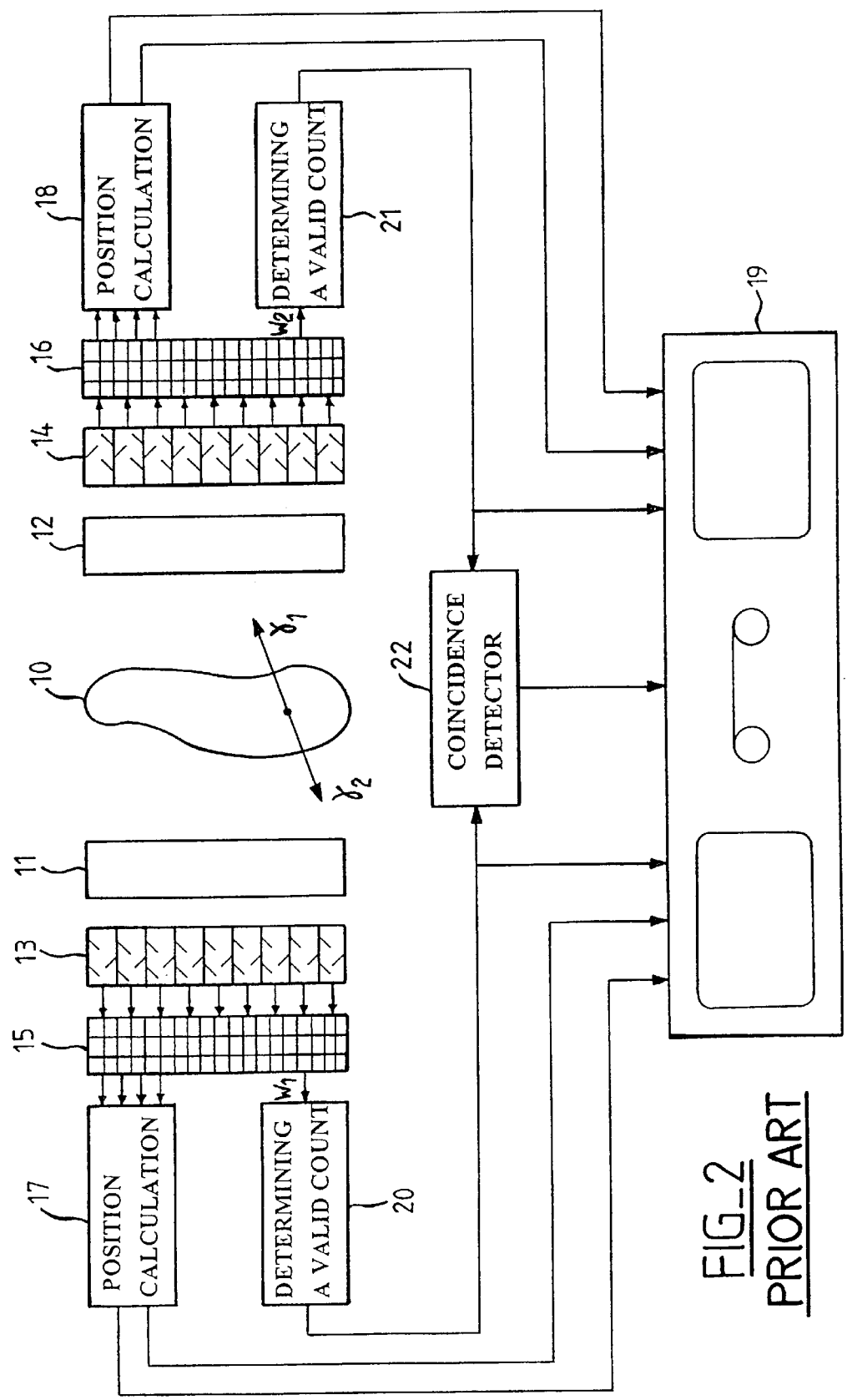
FIG_2
PRIOR ART

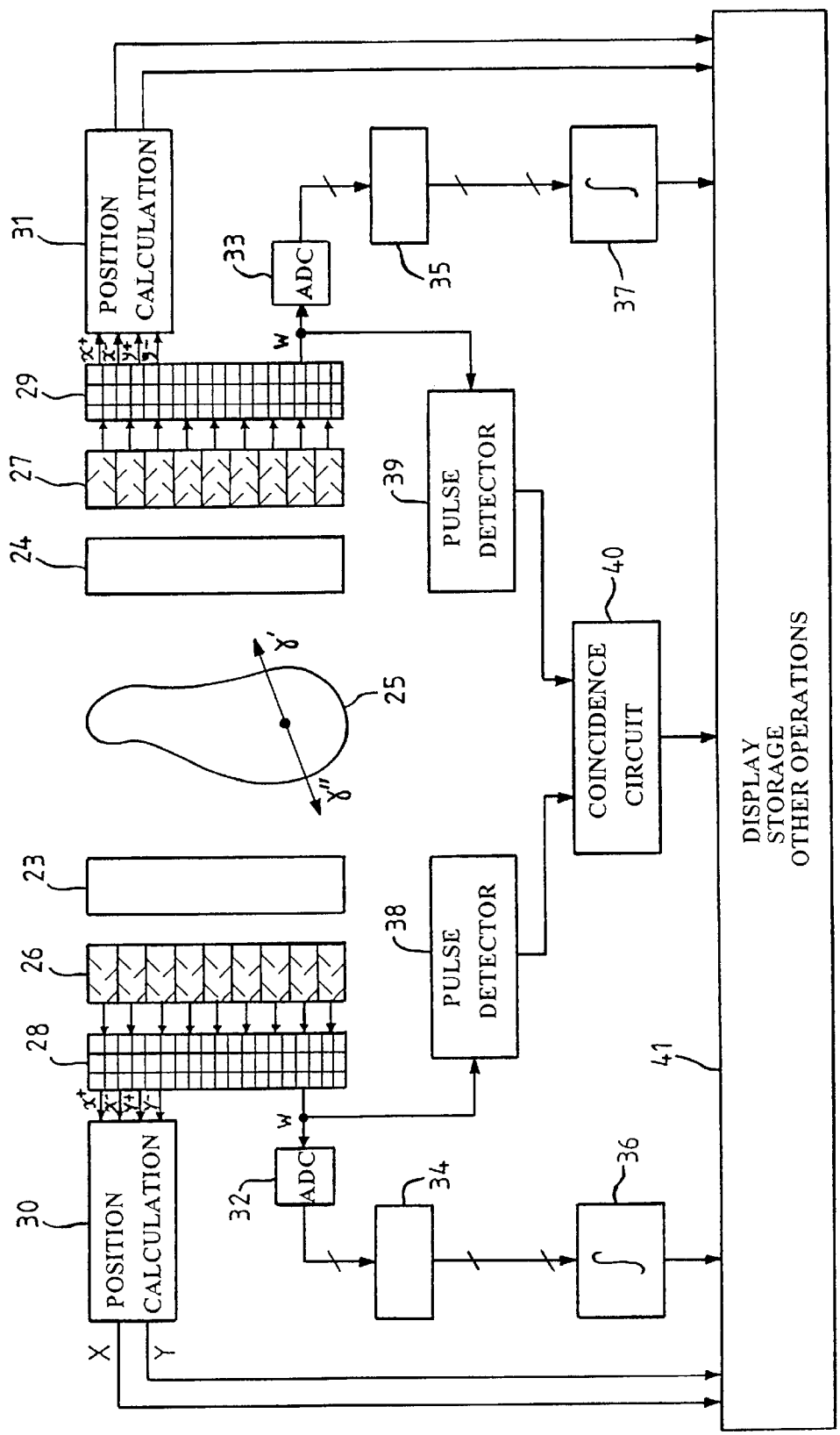
FIG_3

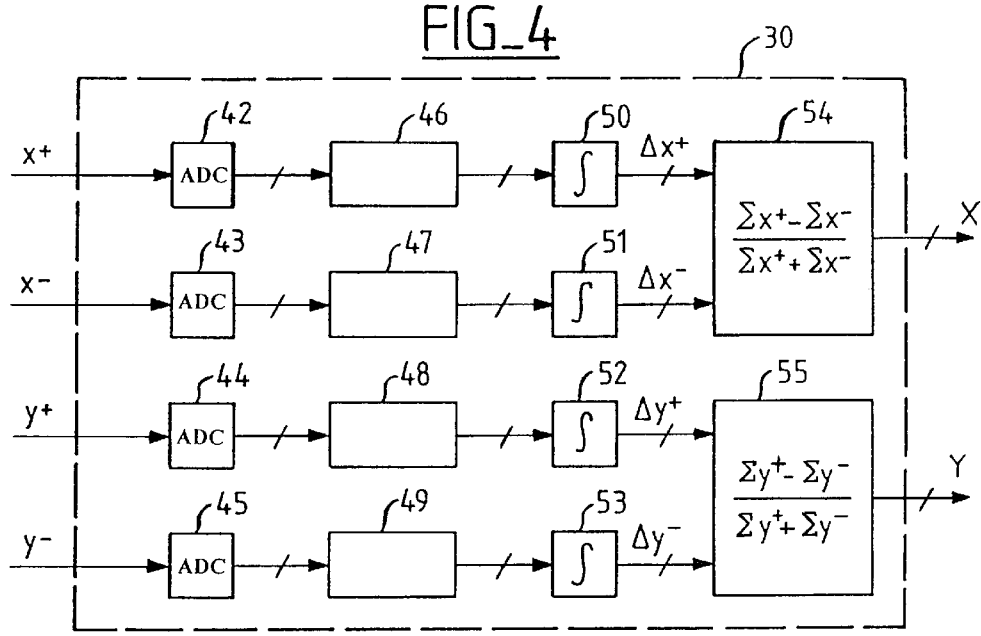
FIG_4
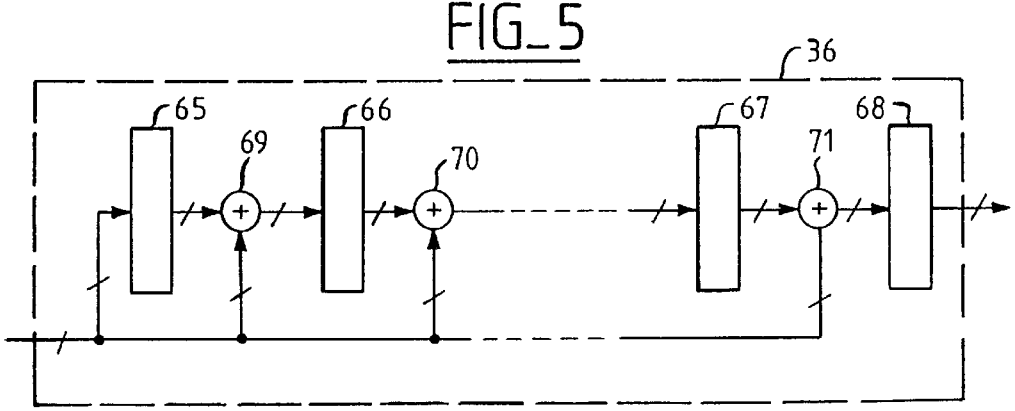
FIG_5
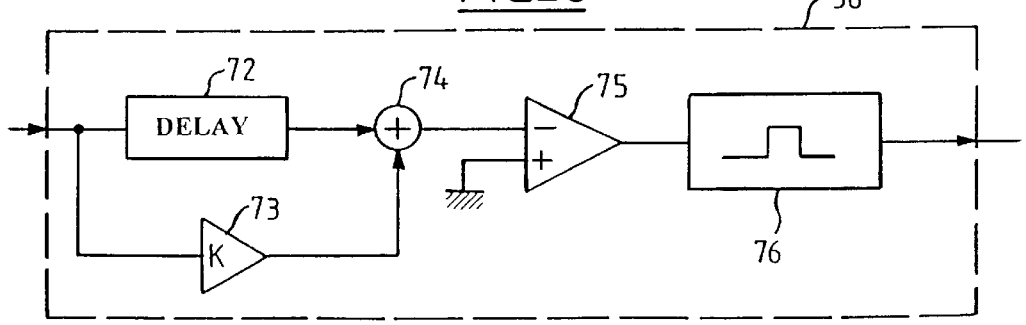
FIG_6

PROCESS FOR PROCESSING PULSES DELIVERED BY A GAMMA CAMERA AND A GAMMA CAMERA USING THIS PROCESS

BACKGROUND OF THE INVENTION

1. Field of the Invention

The invention concerns a process for processing pulses delivered by a gamma camera and a gamma camera using this process. It concerns scintillation cameras or gamma cameras for instance of the ANGER type the American U.S. Pat. No. 3,011,057 of which describes the operating principles and its means of achievement. These gamma cameras are intended to detect and display photons emitted by radioactive bodies.

Gamma cameras are used in nuclear medicine to display in an organ the distribution of molecules marked by a radioactive isotope that has been injected into a patient. The use of gamma cameras can be extended to studying all radioactive bodies.

The operating principle of the gamma cameras is shown on FIG. 1. A radioactive body 1 emits gamma photons γ. These photons are emitted from a point of the body 1, potentially in all directions. A scintillator 2 receives these gamma photons γ and at time of impact converts each gamma photon γ received into a light source s. A set of photomultiplier tubes 3 arranged opposite the scintillator 2 converts into electric signals the light radiation delivered by the source s in the scintillator. Each photomultiplier tube delivers an electrical signal dependent on the total quantity of light that it has received. Weighting arrays 4 (five in general), consisting for instance of impedances of same type convert the signals from the various photomultiplier tubes into five signals $x^+$, $x^-$, $y^+$, $y^-$ and w. Signals $x^+$, $x^-$, $y^+$ and $y^-$ contain information relevant to the X and Y positions of the light distribution barycentre on the detection plane consisting of the photomultiplier tube 3 input faces. The signal w represents the total energy recovered on the set of photomultiplier tubes 3.

A position calculation circuit 5 recovers the signals $x^+$, $x^-$, $y^+$ and $y^-$ to integrate them over a duration equivalent to the duration of a scintillation and to determine the X and Y position of the impact. This position calculation circuit 5 delivers two signals x and y proportional to the X and Y position. An impact detection circuit 6 receives the signal w and determines as a function of this signal w representative of the energy received by the set of tubes 3 a validation signal v which indicates if the impact is to be taken into account or ignored. A display device 7 receives the signals x, y and v and displays or records, if applicable, the X and Y position impact point, an image consisting of the accumulation of impact points. Other measuring devices, without weighting arrays, can be considered. Their principles are to digitise the signals at the output of each photomultiplier tube and to use high-speed microprocessors to make the equivalent calculations. Likewise, the photomultiplier tubes can be replaced by semiconductor devices.

In reality, the radioactive body I emits a certain number of gamma-ray photons γ in a given interval of time commonly known as a number of counts emitted per second. The number of counts emitted per second depends on the activity of the radioactive body 1. In addition, these counts are emitted in a random manner from any point of the radioactive body 1 and in any direction. In fact, to obtain an image, by projection in two dimensions, representative of the radioactive body 1, only the gamma-ray photons γ coming from one direction, for instance normal to the scintillator 2, are of interest. For this, a collimator 8 can be used to collimate the gamma-ray photons γ emitted by the radioactive body 1 on the scintillator 2. This collimator can consist, for instance, of a lead plate several centimeters thick drilled with a multitude of holes oriented for instance perpendicularly to its surface in order to let through only gamma radiations normal to this surface. The effect of adding a collimator is that a sort is made. Indeed, only the photons arriving perpendicularly to the collimator in the example pass through it. This represents one count from around ten thousand.

The counts last only for a very short time and the impact associated with the count is compared to a Dirac function over time. However, the impact on the scintillator 2 triggers a cascade of phenomena through the scintillator 2, the set of photomultiplier tubes 3, the weighting arrays 4 and the connections with the position calculation circuit 5 and the impact detection circuit 6 and finally gives birth to a relatively stretched pulse. To locate the impact, we integrate, into the calculation circuit 5, over a duration representative of the stretched pulse, the signals $x^+$, $x^-$, $y^+$ and $y^-$ so that we can calculate that which corresponds to a barycentre of the light spot received by the set of photomultiplier tubes 3. But, if two counts are very close to each other, the stretched pulses may overlap thus falsifying the impact position calculation.

The aim of the impact detection circuit 6 is to determine whether an impact is to be taken into account. As detection is made at the same time as the impact position calculation, information is supplied to the display device which validates the position associating an energy level with it. Formerly, detection was processed thus:

detection of the exceeding of a noise threshold by signal w, integration of signal w from this detected threshold, detection of the maxima on this signal w, detection of the return of signal w to below the noise threshold thus putting an end to the integration of signal w, generation of a validation signal as a function of the signal w integration result if also signal w is between an authorised maximum and minimum, if only one maximum was detected when signal w was above the noise threshold.

In fact, a detection such as this amounts to checking that the waveform of the energy received corresponds to a certain envelope. This envelope is used to check that there was only one pulse by the detection of a single maximum in a given energy range. Therefore, the low-energy pulses due to the Compton gamma-ray photon diffusion are also excluded.

2. Description of the Related Art

Good control over digital techniques has allowed the system to be improved. In patent request EP-A-0 470 909, a system is described which digitises the signals $x^+$, $x^-$, $y^+$, $y^-$ and w. Then, using a digital filter, the transfer function of which is calculated to be the inverse of the transfer function of the items which convert a photon impact into an electric signal, these signals $x^+$, $x^-$, $y^+$, $y^-$ and w are converted. The digital filtering greatly reduces the pulse duration of the signals. Before filtering, the duration of a pulse is slightly greater than one microsecond. After filtering, this duration may be lower than 250 ns (in fact, the duration depends, among other things, on the sampling frequency and the parameters of the digital filter). As the pulses are shorter, the number of pulse overlaps is lower than before. Under these conditions, more counts can be counted per unit time and, in the end, the images can be acquired more quickly. Detection is nevertheless ensured by an envelope system.

A system with collimator using digital filtering can be used to count up to 200,000 counts per second, which represent an emission of around 2 billion counts per second which corresponds to around 50 to 60 mCi. However, in nuclear medicine, making the patient as radioactive as this with the conventionally used isotopes incurs certain risks for the patient. In general, collimated systems are used with patients to process at most several tens of thousands of counts per second.

Also, we know that position (or positron) emitting isotopes exist where the gamma-ray photons are emitted in pairs in opposite directions, fluor 18 for instance. Another technique for collimating gamma-ray photons, in the case of positions, consists in using a gamma camera with a second detector and a coincidence detection circuit which checks the direction from which the photon emitted in the other direction comes. In general, the gamma camera uses two identical detectors. The coincidence detection circuit is connected to the two detectors of the gamma camera. FIG. 2 shows such a system.

On FIG. 2, a radioactive source 10 emits gamma-ray photons $\gamma 1$ and $\gamma 2$ in pairs in opposite directions. A scintillator, 11 and 12, is placed on each side of the radioactive source 10 to convert the energy of the gamma-ray photons $\gamma 1$ and $\gamma 2$ into light energy. We can see that such a system does not use collimators. The light energy emitted by each of the two scintillators 11 and 12 is received by two sets of photomultiplier tubes 13 and 14 respectively. The sets of photomultiplier tubes 13 and 14 are connected to weighting array assemblies 15 and 16 respectively. The assemblies 15 and 16 each transform the energy recovered from the sets of photomultiplier tubes 13 and 14 respectively into five signals. Four signals are used to locate the impact of the gamma-ray photon $\gamma 1$ or $\gamma 2$ on the scintillator 11 or 12, a fifth signal (W1 or W2) being representative of the total energy given off by the gamma-ray photon $\gamma 1$ or $\gamma 2$. The respective position calculation circuits 17 and 18 each recover the four signals, from the weighting arrays 15 and 16, which are representative of the position of the impact to calculate the coordinates of the impact point and to transmit them to a display and storage device 19. Another calculation circuit locates the origin of the two gamma radiations $\gamma 1$ and $\gamma 2$. Variants are possible at detector level; the signals can be digitised at the output of the photomultiplier tubes making the arrays unnecessary; the multiplier tubes can also be replaced by equivalent devices.

The impact detection circuits 20 and 21 recover the signal W1 and W2, respectively representative of the total energy from the array assemblies 15 and 16 respectively. These impact detection circuits 20 and 21 will, on the one hand, check that the count is valid, that is in compliance with the envelope and, on the other hand, calculate the power integral for each valid count. A validation signal, if the count is valid, will then be transmitted to the display device 19 and to a coincidence detector 22. If two valid events arrive at the same time, that is in a time window of for instance around 10 nanoseconds, the coincidence detector 22 will emit a binary signal to indicate to the display device 19 that there is indeed a coincidence. The display system 19 can reconstruct the paths of the photons and then the images.

With a patient, the gamma-ray photon emissions are made in all directions sometimes at the same time. Under clinical conditions, the detectable coincidences in general represent only 1% of the counts received by the scintillators 11 and 12. 99% of the counts received are single, that is, only one of the two photons emitted touches a gamma camera detector. In practice, gamma cameras using coincidence measure several hundred thousand counts per second which amounts to detecting and recording several thousand coincidences per second. The advantage over a collimator device lies mainly in the reduction of the radioactive dose to be used in the patient. The dose injected into the patient is 100 times less radioactive for an equivalent acquisition time.

An article by Mankoff, Muehllehner and Karp, published in Phys. Med. Biol., 1989, Vol. 34, No. 4, pages 437–456 and entitled "The high count rate performance of a two-dimensionally position-sensitive detector for positron emission tomography" mentions high-speed counting using coincidence. This article mentions the counting of two million counts per second using digital processing allowing a count to be processed in less than 250 ns. Nevertheless, at two million counts emitted per second, it is only possible to recover 62% of the counts which are however emitted experimentally to produce a coincidence for each count emitted. The other 38% correspond to counts not separated timewise by the gamma camera used. If we increase the count emission rate, the percentage of usable counts would be lower still.

If we transpose the device mentioned in the article above to medical use with a patient, the number of counts received and usable in coincidence must be divided by one hundred.

Whatever the case, increasing the number of counts emitted by the patient tends to make the counts received overlap and therefore reduces the number of valid counts beyond a certain number of counts emitted of around two million.

Examinations using gamma cameras are relatively long as they require the acquisition of images each requiring a high number of counts (to obtain a well defined image, several million counts may be required). A factor allowing a reduction in the examination time is to increase the number of counts to be taken into account per second. However, at present, the technology limits the number of counts to be accepted.

To sum up, the state of the art is as follows:
  the gamma camera of FIG. 1 using a collimator does not allow the measurement of more than several tens of thousands of counts per second on a patient even though, technologically it is quite possible of accepting 200,000 counts per second; it also requires the injection of a highly active isotope into the patient,
  the gamma camera in FIG. 2 using a coincidence detection system allows a significant reduction in the doses of radioactive products to be absorbed by the patient by slightly reducing the number of counts taken into account (doses 100 times less for an equal number of counts), nevertheless, as we saw in the above mentioned article, with high activities of around 2 million counts, more than 30% of the usable counts are lost; such a system allows the recovery of around 14,000 counts out of 2 million, also the spatial resolution is in general better than with collimated systems.

OBJECTS AND SUMMARY OF THE INVENTION

The aim of the invention is to increase the number of acceptable counts for a coincidence detection gamma camera without the need for significant technological changes or, especially, increasing the radioactivity dose to be injected into the patient. The invention combines detection by coincidence with a compression of the signals received, for instance by deconvolution, to shorten the duration of the pulses corresponding to the impact of a gamma-ray photon on a detector, the coincidence detection being achieved on the signals before deconvolution without check of the validity of the count using an envelope. The result is a certain error due to the missing tests which can be partially compensated for by a minimum energy threshold. But, due to the fact that the counts are better spaced out in time, we can satisfy ourselves by simply detecting simultaneity.

Thus the invention proposes a process for processing the signals delivered by a gamma camera including two detectors placed on either side of a radioactive body, each of the said detectors producing analogue electric signals consisting of pulses relative to gamma-ray photon impacts on the said detectors, wherein for each detector:

it is produced at least one compressed signal, each compressed signal being representative of one of the electric signals on which the duration of the pulses has been shortened;

it is calculated the coordinates of the impact point from the compressed signals;

and in that in parallel:

it is detected the pulses on at least one analogue electric signal of each detector;

it is produced a coincidence signal if a pulse is detected, in a time window associated with the simultaneity, on at least two of the analogue electric signals delivered respectively by the two detectors.

Such a process uses, in certain cases, faulty data (fortuitous coincidences and overlapping of pulses) which goes against that which was sought up until the present time. In the invention, it has been discovered that this process allows the recovery of data with a low error rate which is quite acceptable for tomography. Completely erroneous data are of course taken into account; this leads to added noise or blur on the recovered image. The noise which corresponds to the fortuitous coincidences increases linearly with the increase in the activity of the body. It is possible to increase the activity of the patient without reducing the rate of usable coincidences; an increase in noise is to be expected on the image.

The subject of the invention is also a gamma camera including two detectors each producing analogue electric signals relative to the impacts of gamma-ray photons on the said detectors, wherein the said gamma camera includes: compression means to compress the pulses on the analogue electric signals and deliver compressed signals, means for detecting the presence of pulses on at least two of the analogue electric signals associated respectively with the two detectors, coincidence means for detecting whether the pulses of at least two analogue electric signals occur in a defined time window.

For the process or the gamma camera, improvements are possible.

Preferably, we use digitised data in order to simplify the design of the gamma camera. Digital filtering with a transfer function corresponding to the inverse of the transfer function of one of the detectors is used.

Also, rather than triggering position calculations and signal integrations when we consider that the count received is valid, it will be preferred an architecture allowing an operation to be triggered at each clock cycle thus performing several operations simultaneously but offset by one clock cycle, independent of the coincidence detection.

BRIEF DESCRIPTION OF THE DRAWINGS

The invention will be easier to understand and the advantages will become clearer on reading the description, non restrictive, which will follow and which is to be read in conjunction with the appended drawings on which:

FIG. 1 shows a schematic diagram of a collimator gamma camera according to the previous state of the art, FIG. 2 shows a schematic diagram of a coincidence gamma camera according to the previous state of the art, FIG. 3 shows a schematic diagram of a preferred design of a gamma camera according to the invention, FIGS. 4 to 6 show a schematic diagram of the preferred designs for the circuits used in the preferred design of the gamma camera of FIG. 3.

Figure 7:
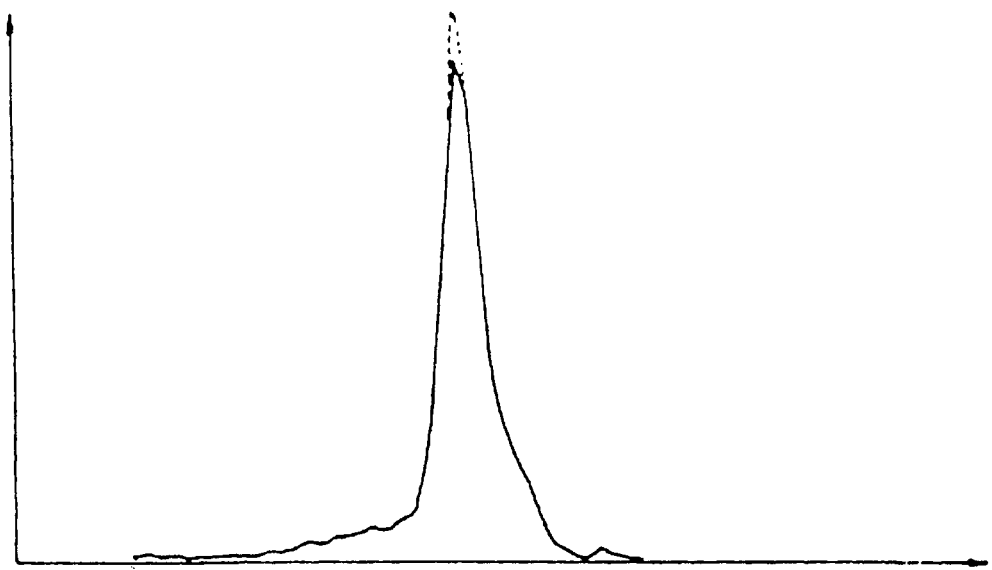
FIG. 7 shows a pulse response, its FOURIER transformation and the opposite transformation, according to the previous state of the art.

As FIGS. 1 and 2 have already been described, we will not describe them in more detail.

DESCRIPTION OF THE PREFERRED EMBODIMENTS

FIG. 3 represents a non-restrictive design of the invention. On this figure, we can see two scintillators 23 and 24 placed on either side of a radioactive body 25, a position emitter, which emits gamma-ray photons $\gamma'$ and $\gamma''$ in pairs which are emitted in opposite directions. In practice, 1% of the pairs have two photons which reach the two scintillators. In addition, the photons $\gamma'$ and $\gamma''$ are emitted randomly in place, direction and frequency according to a law which depends on the radioactivity density of the radioactive body. When a photon $\gamma'$ or $\gamma''$ comes into contact with a scintillator 23 or 24, the scintillator converts the energy of the photon into light energy which leaves in all directions. The light energy emitted by the scintillator 23 or 24 is recovered by a set of photomultiplier tubes 26 or 27, each scintillator 23 or 24 having a set of photomultiplier tubes 26 or 27 associated with it. Each of the photomultiplier tubes of each set 26 or 27 delivers an electric signal proportional to the quantity of light received from the scintillator which itself is dependent on the position of the tube to be considered in relation to the impact of the photon $\gamma'$ or $\gamma''$ on the scintillator 23 or 24.

In the preferred design, it is used two weighting array assemblies 28 and 29 consisting for instance of resistors which are connected to the two sets of photomultiplier tubes 26 and 27 respectively. Each weighting array assembly 28 or 29 consists of five arrays weighting differently the signals delivered by each photomultiplier tube of the set of photomultiplier tubes 26 or 27 associated with the array assembly 28 or 29. The weightings made by each of the array assemblies 28 or 29 deliver five signals $x^+$, $x^-$, $y^+$, $y^-$ and w directly dependent on the instantaneous quantity of light given off by the scintillator 23 or 24. Signals $x^+$, $x^-$, $y^+$ and $y^-$ are representative of the distribution of the light spot caused by the impact of the photon $\gamma'$ or $\gamma''$ on the scintillator 23 or 24 along the X and Y axes of the scintillator 23 or 24 to be considered. The signal w is representative of the total light energy given off by the scintillator 23 or 24 after the impact of the photon $\gamma'$ or $\gamma''$.

The preferred design of the detectors has been chosen as it is the most well known at the present time and therefore the simplest to understand by a person skilled in the art. Of course, other systems exist to which the invention is applicable which are more or less effective depending on their state of development. There exist for instance systems without arrays where a signal digitisation is achieved directly at the output of each photomultiplier tube, the invention requires an output branch from one or more photomultiplier tubes in order to recover the analogue signals. Systems also exist where the photomultiplier tubes are replaced by equivalent semiconductor devices.

In the remainder of this document, it will be called detector or detection head the device consisting for instance of a scintillator 23 (or 24), a set of photomultiplier tubes 26 (or 27) and a weighting array assembly 28 (or 29).

Two position calculation circuits 30 and 31 are connected to two weighting array assemblies 28 and 29 respectively. Each of the position calculation circuits 30 or 31 receives signals $x^+$, $x^-$, $y^+$ and $y^-$. The aim of these calculations circuits 30 and 31 is to determine the position of the impact of a photon from the four signals received. Many designs of this type of circuit are known, both analogue and numerical, and can be used with the invention. However, a digital processing circuit will be preferred. It will be described later the circuit of FIG. 4 which is one example of a possible design for one of these position calculation circuits 30 and 31. Each of the calculation circuits 30 and 31 delivers two pieces of information X and Y. In the example, information X Y are supported by two 16-bit buses; this information can however be coded over another number of bits or even be analogue.

If the signals are directly digitised at the output of each photomultiplier tube, one bus may be sufficient to allow all the photomultiplier tubes to communicate with the calculation circuits which will be of course adapted to suit. In addition, the energy of the count received can also be calculated in these same calculation circuits.

Figure 8:
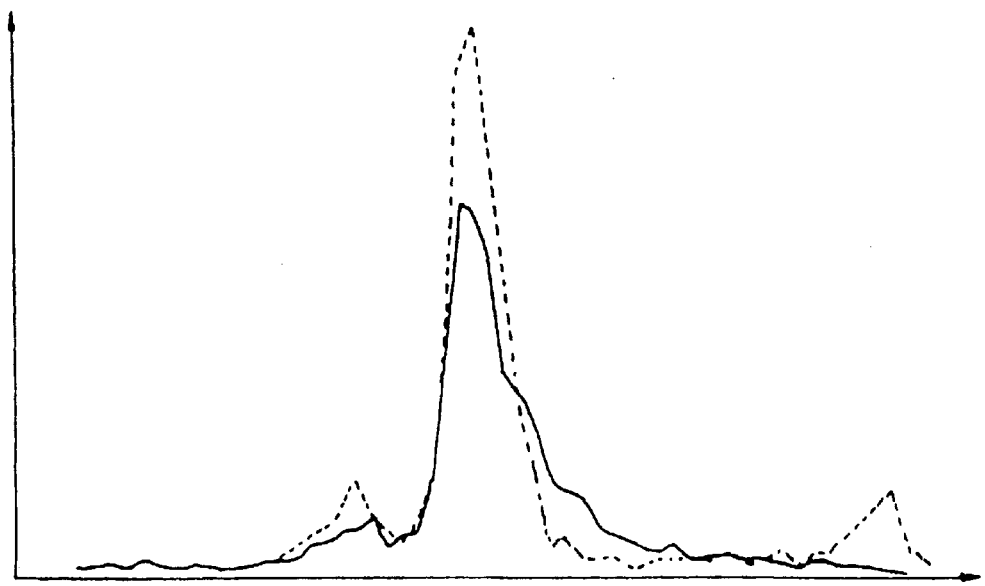
FIG. 8 shows an inverse transformation function, according to the previous state of the art.

Two analogue/digital converters 32 and 33 are connected to the weighting array assemblies 28 and 29 respectively to convert the signals w into energy digital information coded over 16 bits in our example. Two deconvolution circuits 34 and 35 are connected to the analogue/digital converters 32 and 33 respectively. These deconvolution circuits 34 and 35 are in fact digital filters of a conventional structure the transfer function of which is the inverse of the transfer function of the elements converting the impact of a photon γ' (or γ") on the scintillator 23 (or 24) into an electric signal w (which in the remainder of this document will be called the initial transfer function). This transfer function can be obtained for instance by calculating the inverse Fourier transform of the inverse of the Fourier transform of the initial transfer function. For this, it is considered that the Fourier transform of the initial transfer function is equal to the Fourier transform of the pulse response to an impact of a photon γ' (or γ"). For more information, one can refer to document EP-A-0 470 909 and, particularly, the following material from that document pertaining to transfer functions (FIGS. 7 and 8). Thus, all the pulses shall be taken into account without any resultant degradation of spatial resolution.

The calculation of the inverse transfer function h−1(t) results from conventional considerations for signal processing. Knowing that the FOURIER transformation of a convolution product is the product of the FOURIER transformations, it is possible to write:

$$S(f)=E(f) \times H(f)$$

where S(f), E(f) and H(f) are respectively the FOURIER transformations of s(t), e(t) and h(t) and where the sign x represents the usual multiplication operation.

Thus, $$E(f)=S(f) \times 1/H(f).$$

With reference again to the convolution product:

$$e(t)=s(t)*TF-(1/H(f))$$

where TF−1 represents the inverse FOURIER transformed operation.

Thus, the inverse transfer function h−1(t) where 1 is sought is equal to the inverse FOURIER transform of the inverse of the FOURIER transform of the initial transfer function:

$$h-1(t)=TF-1(1/H(f)).$$

The convolution of the signal s(t) by h−1(t) shall thus reprovide the initial signal e(t):

$$e(t)=s(t)*h-1(t).$$

Knowing the transfer function h−1(t), the technician is able to embody a digital filter having the appropriate coefficients.

In practice, this filter could be refined by apodizing it. This operation is effected by multiplying 1/H(f) by a function having a value close to one unit for the low and average frequencies and close to zero for the high frequencies. Thus, the high frequencies generally carried by electronic noise are suppressed.

By simulating signals appearing at various points of the circuits of a gamma camera, the inventors have been able to determine the various functions involved in the invention, these functions being illustrated on FIGS. 7 and 8.

FIG. 7 firstly shows on portion a transfer function h(t) which expresses the pulse response of the circuits of a gamma camera (scintillator, photomultiplier, resistors, transmission).

Portion b shows the corresponding FOURIER H(f) transform.

Portion c shows the inverse I/H(f).

FIG. 8 shows an inverse FOURIER transform of 1/H(f), namely h−1(t), which is a transfer function of the sought-after filter.

Two integrators 36 and 37 are connected to an output bus of each of the deconvolution circuits 34 and 35 respectively. These integrators 36 and 37 have a structure allowing them to sum several successive information values output by the deconvolution circuits 34 and 35. Also these integrators 36 and 37 start and finish at each clock cycle an integral limited according to the Riemanns method to a certain number of clock cycles. These two integrators 36 and 37 deliver data at their respective outputs, coded for instance over 16 bits, which is representative of the total power received by the set of photomultiplier tubes 26 or 27 during a finite period; this data can be, in certain cases, representative of the energy of an impact received by a detector.

Two pulse detector circuits 38 and 39 are also connected to the weighting array assemblies 28 and 29 respectively to receive the analogue electric signals w. Each of these pulse detector circuits 38 or 39 delivers a binary signal representative of the presence of a pulse on the analogue electric signals w by positioning itself in a first state or in a second state.

If a signal from a single photomultiplier tube (preferably located in the centre of detector) is used, we recover the same train of pulses but their amplitudes are smaller and variable according to the distance between the impact point of the photon and the position of the photomultiplier tube. The pulse detector must be more sensitive.

A coincidence circuit 40 recovers the two binary signals delivered by the two pulse detector circuits 38 and 39. This coincidence circuit 40 sets a binary signal to a first state if there is coincidence and to a second state if there is no coincidence. In other words, if the two pulse detector circuits 38 and 39 simultaneously indicate a pulse in a given time window, the coincidence circuit 40 then indicates a coincidence, a simple logic gate with two inputs adapted to the selected states being sufficient. The logic gate output signal can be conditioned, for instance, by means of a monostable circuit.

A storage circuit 41 receives from the position calculation circuits 30 and 31 the coordinates of the impact points on each scintillator at each clock period and the energy associated with each of these points. However, almost all points received are false. The binary signal indicating the coincidence will determine if the points must be stored or not. Attention must however be paid to the synchronisation of the information arriving from the various circuits 30, 31, 36, 37 and 40. Indeed, the synchronisation will depend on the sampling frequency and the rate of the digital elements, the accuracy of the deconvolution circuits and the number of cycles on which the various signals will be integrated.

The storage circuit 41 can also do a rapid sort of the valid impacts by using a minimum energy threshold to eliminate errors due to high scatter.

In the storage circuit 41, the valid points to which the energies are associated are therefore stored and possibly displayed or processed. Image processing, indispensable to obtain a clear image, consists in reconstructing the paths (for example identified by spherical coordinates) according to the impact points on each of the detectors. From the paths, various images are constructed by straight projection onto planes perpendicular to the direction of the path and passing via a central point of the body under examination. It is also possible to submit the image obtained to various processes such as elimination of noise, addition of contrast or reconstruction in three dimensions, or other various and varied image processes that need not be explained within the scope of the invention.

FIG. 4 shows a preferred design of the position calculation circuits 30 and 31. Thus, the position calculation circuit 30 has four inputs for the signals $x^+$, $x^-$, $y^+$ and $y^-$. An analogue/digital converter 42 to 45 of same type as the converters 32 and 33 is connected to each of the inputs. Each of these converters 42 to 45 is connected via a bus to the input of one of the deconvolution circuits 46 to 49. Each of these deconvolution circuits 46 to 49 is the same as the deconvolution circuits 34 and 35. At the output of these deconvolution circuits 46 to 49, informations are recovered to be introduced into the integrators 50 to 53. The integrators 50 to 53 being of same type as integrators 36 and 37. An X position calculation circuit 54 is connected to the output of the two integrators 50 and 51 which are connected to the signals $x^+$ and $x^-$. This calculation circuit 54 delivers at its output information for instance equal to $X=(\Sigma x^+ - \Sigma x^-)/(\Sigma x^+ + \Sigma x^-)$, where $\Sigma x^+$ and $\Sigma x^-$ are data output by integrators 50 and 51 which correspond to signals $x^+$ and $x^-$. A Y position calculation circuit 55 is connected to the output of the two integrators 52 and 53 which are connected to the signals $y^+$ and $y^-$. This calculation circuit 55 delivers at its output information equal to $Y=(\Sigma y^+ - \Sigma y^-)/(\Sigma y^+ + \Sigma y^-)$, where $\Sigma y^+$ and $\Sigma y^-$ are data output by integrators 52 and 53 which correspond to signals $y^+$ and $y^-$.

Other calculation possibilities can be considered for calculating the coordinates of the impact on the detector. Likewise, different design possibilities for the calculation circuits 54 and 55 are possible. Preferably, microprogrammed circuits generally known under the name of DSP (which stands for Digital Signal Processor) are used.

FIG. 5 shows the preferred design for integrators 36, 37, 50 to 53. The integrator 36 consists of a certain number of registers 65 to 68 equal to the number of sampling periods to be taken into consideration to calculate the integral; in practice, there will be 8 to 10 periods and therefore 8 to 10 registers. Between registers 65 and 68, parallel adders 69 to 71 have been placed, there is one adder 69 to 71 less than the registers 65 to 68. Each of the adders 69 to 71 receives data from the output of the previous register 65 to 67 and data from the input of the integrator 36 to deliver a result at the input of the next register 66 to 68. The first register 65 of the chain has its input connected to the input of the integrator 36 and the last register 68 of the chain has its output connected to the output of the integrator 36. The advantage of such a set-up is that integration can be started at each clock cycle without the need to know if the calculation is valid or not. In order to remain within a 16-bit format, the LSB (least significant bit) at the output of the adder 69 to 71 is not recovered in the next register 66 to 68. If a very effective DSP is used, it is possible to implement the integrators above.

FIG. 6 shows the preferred design for the pulse detector circuits 38 and 39.

The input of the detector circuit 38 is connected, on the one hand, to the input of a delay circuit 72 and, on the other hand, to the input of an inverting attenuator 73. The delay circuit 72 can consist, for instance, of a delay line which delays the signal by several nanoseconds between its input and an output. The inverting attenuator 73 corresponds to a linear amplifier with an input and an output which amplifies the input signal by a factor K, K being between 0 and −1. An analogue adder 74 with two inputs and one output has its first input connected to the output of the delay circuit 72 and its second input connected to the output of the inverting attenuator 73. A comparator 75 with two inputs and one output has a first input connected to the 0 V and a second input connected to the output of the analogue adder 74. Items 72 to 75 form a circuit equivalent to a constant fraction discriminator. The output of the comparator 75 is in a first state if there is no pulse then changes to a second state as soon as the signal is subjected to a positive variation with a slope greater in absolute value than K times the previous voltage divided by the delay caused by the delay circuit 72. The output of the comparator 75 returning to the first state if the slope becomes lower or is inverted or if the slope is maintained beyond the delay caused by the delay circuit 72. In this way, practically all pulses are detected. A monostable circuit 76 with one input and one output has its input connected to the output of the comparator 75, its output being combined with the output of the detector circuit 38. The monostable circuit 76 converts the output signal of the comparator 75 into a binary-type logic signal. Each detection of a pulse on the input signal of the circuit 38 leads to a change in state of the binary signal at the output of monostable 76 for a predefined time, for instance around 10 nanoseconds. The monostable circuit 76 opens a time window of a predefined duration.

Variants can be considered by using for instance maximum detectors, consisting for instance of a branch circuit followed by zero detection, the whole conditioned by a monostable circuit.

This preferred design is the result of many trade-offs. Many different designs can be made without leaving the scope of the invention for instance processing the information over a different number of bits, not performing the truncations stated, using circuits which perform the operations in a different number of cycles, or not using the same logical levels. The items comprising the preferred design of the invention must in fact be considered in a functional manner and do not limit the invention to this preferred design.

It is also possible to deviate a little from the preferred design without deviating from the subject of the invention. Certain choices made for the preferred design are not mandatory. Indeed, it is possible to have a completely analogue device which makes the deconvolution filter calculation more complex.

In the preferred design, we use four location signals and a signal relevant to the energy. It is quite possible to use a different number of signals without deviating from the invention, for example a total of 4 or 6 signals can be considered (for this, the number of arrays on each detector will have to be modified). In addition, we have chosen to detect a part of the positive-going edges of the pulses on a signal representative of the energy whereas it is possible to detect the pulses on one of the location signals or even on a signal delivered directly by a photomultiplier tube or equivalent. It is even possible to make redundant detection by detecting pulses on several signals delivered by each detection head.

The use of the array assembly in a detection head can be replaced by an equivalent device which performs a sampling operation and a digital conversion at the output of each photomultiplier tube. High-speed microprocessors will then be in charge of performing the position and energy calculation.

Also, the digital filtering the aim of which is to perform a deconvolution can be replaced by any other signal processing algorithm or filtering which performs a time separation of the pulses by compressing the pulses.

We claim:

1. A method for processing signals delivered by a gamma camera including two detectors arranged on either side of a radioactive body, each of the detectors generating a plurality of first and second analogue electric signals each comprised of a pulse relevant to an impact of one of a corresponding pair of gamma-ray photons ($\gamma'$ and $\gamma''$) on an associated one of the detectors, each first analogue electric signal being indicative of a position of the impact and each second analogue electric signal being indicative of an energy level of the impact, the method comprising the steps of:

producing, for each detector, at least one compressed signal each compressed signal corresponding to one of the first and second analogue electric signals generated in response to the impacts;

calculating the coordinates of the position from the compressed signals corresponding to the first analogue electric signals;

and that in parallel to said producing and calculating steps:

detecting a coincidence pulse associated with at least one analogue electric signal of each detector;

generating a coincidence signal if the coincidence pulses are detected in a predetermined time window, wherein the coincidence signal validates the corresponding positions of the impacts.

2. The method in accordance with claim 1, wherein the first and second analogue electric signals delivered by the detectors are weighted by the weighting array assemblies associated with each of the detectors.

3. The method in accordance with claim 2, wherein the coincident pulses correspond to the second analogue electrical signals.

4. The method in accordance with claim 3, further comprising the steps of, at each clock period:

integrating the compressed first and second analogue electric signals over a predetermined number of the periods, and calculating the corresponding positions of the impacts of the corresponding pair of gamma ray photons ($\gamma'$ and $\gamma''$) on the detectors from the compressed signals which were integrated over the predetermined number of periods.

5. The method in accordance with claim 1, wherein the compressed signals are obtained by filtering according to a second transfer function generally equal to the inverse of a first transfer function corresponding to the conversion of the gamma-ray photons ($\gamma'$ and $\gamma''$) into the first and second analogue electric signals.

6. A gamma camera including two detectors each producing first and second electric signals each comprised of a pulse relevant to an impact of one of a corresponding pair of gamma-ray photons ($\gamma'$ and $\gamma'$) on a corresponding one of the detectors, the gamma camera comprising:

first and second compression means for correspondingly compressing the first and second electric signals;

a means for detecting the presence of pulses of at least two electric signals associated respectively with the two detectors;

a coincidence means for detecting whether the pulses of the at least two electric signals are produced in a predetermined time window;

analogue/digital converters to convert the first and second electric signals into digital signals, and wherein the first and second compression means each comprise digital filters; and a pair of calculation circuits to generate position signals indicative of the position of the impacts of the corresponding pair of gamma-ray photons on the corresponding detectors, and wherein said calculation circuits have an architecture configured to start a calculation and to finish another calculation at each period of a clock which synchronizes the operation of said calculation circuits.

7. A method of processing signals detected by a gamma camera, the method comprising:

using two detectors arranged on either side of a radioactive body, each of the detectors generating a plurality of first and second analogue electric signals, each comprised of a pulse, in response to an impact of one of a corresponding pair of gamma-ray photons ($\gamma'$ and $\gamma''$) on a corresponding one of the detectors, wherein each first analogue electric signal is indicative of a position of the impact and each second analogue electric signal is indicative of an energy level of the impact;

compressing the first and second electric signals;

calculating the coordinates of the position based on the first compressed signals; and that in parallel with said compressing and calculating steps:

detecting a coincidence pulse associated with at least one second analogue electric signal generated by each detector;

generating a coincidence signal if said coincidence pulses are detected in a predetermined time window, wherein the coincidence signal validates the corresponding positions of the impacts.

8. A method in accordance with claim 7, wherein said detecting step is performed by using a detector circuit including a constant fraction discriminator and a monostable circuit.

9. The method in accordance with claim 7, wherein the compressed signals are obtained by filtering according to a second transfer function generally equal to the inverse of a first transfer function, said first transfer function corresponding to the conversion of the gamma-ray photons (γ' and γ") into the first and second electric signals.

10. The method in accordance with claim 7, wherein the coincident pulses correspond to the second analogue electrical signals.

11. The method in accordance with claim 10, further comprising the steps of, at each clock period:
- integrating the compressed first and second analogue electric signals over a predetermined number of the periods, and
- calculating the corresponding positions of the impacts of the corresponding pair of gamma ray photons (γ' and γ") on the detectors based on an output of said integrating step.

12. A gamma camera comprising:
- a pair of detectors each producing first and second electric signals, each signal comprised of a pulse corresponding to an impact of one of a corresponding pair of gamma-ray photons (γ' and γ') on a corresponding one of the detectors;
- first and second compression circuits that correspondingly compress the first and second electric signals;
- a pulse detector that detects the presence of pulses of at least two electric signals associated respectively with said pair of detectors;
- a coincidence circuit that determines whether the pulses of the at least two second electric signals, are produced in a predetermined time window;
- at least one analogue/digital converter to convert the first and second electric signals into digital signals, and wherein the first and second compression circuits each comprise digital filters; and
- a pair of calculation circuits to generate position signals indicative of the position of the impacts of the corresponding pair of gamma-ray photons on the corresponding detectors, and wherein said calculation circuits have an architecture configured to start a calculation and to finish another calculation at each period of a clock which synchronizes the operation of said calculation circuits.

13. A gamma camera in accordance with claim 12, wherein said coincidence circuit generates a coincidence signal in response to only a determination that said electric signals are produced in the predetermined time window.

14. A gamma camera comprising:
- a pair of detectors each producing first and second electric signals, each signal comprised of a pulse corresponding to an impact of one of a corresponding pair of gamma-ray photons (γ' and γ') on a corresponding one of the detectors;
- first and second compression circuits that correspondingly compress the first and second electric signals;
- a pulse detector that detects the presence of pulses of at least two electric signals associated respectively with said pair of detectors;
- a coincidence circuit that (1) determines whether the pulses of the at least two second electric signals are produced in a predetermined time window, and (2) generates a coincidence signal in response to only a determination that said electric signals are produced in the predetermined time window; and
- wherein the camera generates the coincidence signal in parallel with calculating the coordinates of a position of one of the impacts based on the compressed first electric signals.

* * * * *